United States Patent [19]

Kurtin

[11] Patent Number: 4,900,597

[45] Date of Patent: Feb. 13, 1990

[54] IMAGE TRANSFER LABEL

[76] Inventor: Stephen Kurtin, 3835 Kingswood Rd., Sherman Oaks, Calif. 91403

[21] Appl. No.: 138,348

[22] Filed: Dec. 28, 1987

[51] Int. Cl.[4] ........................ A61F 13/02; E04F 15/16; B32B 3/26; B44C 1/16

[52] U.S. Cl. ........................................ 428/41; 428/132; 428/313.5; 428/21.5; 428/402.2; 156/236; 156/241

[58] Field of Search ........................ 428/40, 41, 42, 81, 428/202, 203, 204, 205, 352, 914, 918, 355, 354, 132, 134, 313.5, 321.1, 321.5; 40/594, 595, 611, 630; 283/100, 101, 103, 104, 105, 45; 284/1 R

[56] References Cited

U.S. PATENT DOCUMENTS

| | | | |
|---|---|---|---|
| 2,603,899 | 7/1952 | Leander | 156/248 |
| 2,783,910 | 3/1957 | Johnson | 156/241 |
| 3,376,182 | 4/1968 | Borell et al. | 156/235 |
| 3,897,587 | 2/1974 | Molner | 156/241 |
| 3,950,580 | 4/1976 | Boudet | 428/41 |
| 3,973,788 | 8/1976 | Pekko et al. | 282/1 R |
| 3,974,311 | 8/1976 | Cherrin | 40/2 R |
| 4,624,875 | 11/1986 | Watanabe et al. | 428/204 |

FOREIGN PATENT DOCUMENTS

| | | | |
|---|---|---|---|
| 94845 | 5/1982 | European Pat. Off. | 156/240 |

*Primary Examiner*—Michael W. Ball
*Assistant Examiner*—Louis Falasco
*Attorney, Agent, or Firm*—Saul Epstein

[57] ABSTRACT

A label which can be applied to envelopes or the like as an address label. The label, which is transparent, has an area treated so that it will detach a fused toner image from a carrier sheet printed xerographically or by a laser printer and cause the image to adhere to the label. Adhesive or chemical means are used to cause the image to transfer. In use, the label is first applied to a carrier sheet, on which is printed, the desired image, such as an address. When the label is removed from the carrier sheet, the fused toner image remains adhered to the label's underside, and the label can then be applied to an envelope. The label, being transparent, displays the image.

9 Claims, 1 Drawing Sheet

FIG. 1
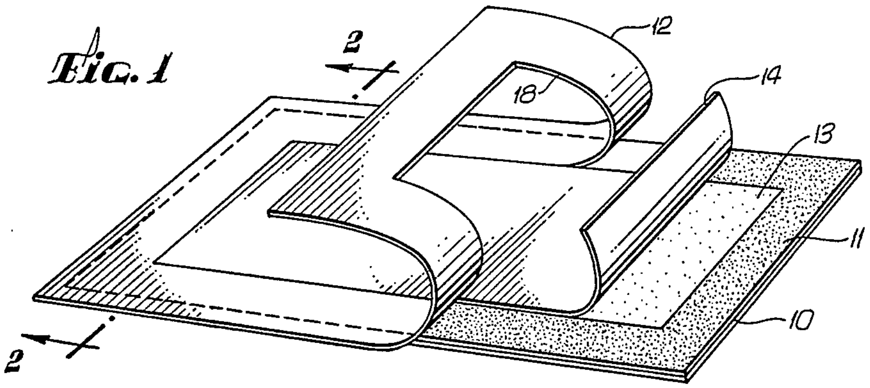
FIG. 2
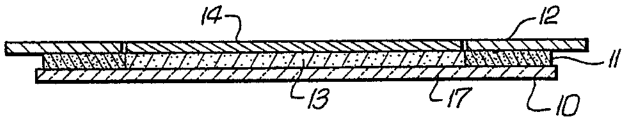
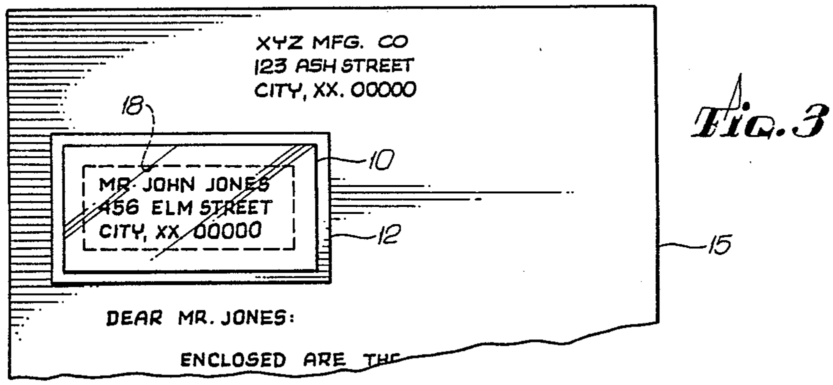
FIG. 3
FIG. 4
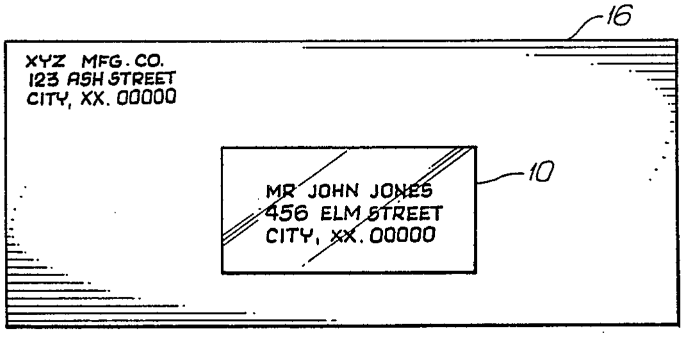
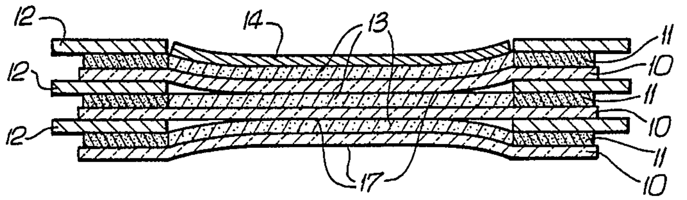
FIG. 5

IMAGE TRANSFER LABEL

BACKGROUND OF THE INVENTION

Until recently, the addressing of envelopes in a business environment created no particular difficulty. An envelope was merely placed in a typewriter and the address typed. With the advent of automatic typewriters, this became even easier. After the envelope was inserted in the typewriter, the address as it appeared on the letter was "selected" and automatically typed onto the envelope. Increasingly, however, letters are being "typed" on computers which are coupled to laser printers rather than impact printers. Unfortunately, present day laser printers are not well suited for printing on envelopes. There is typically no bin available for envelopes on a laser printer so that they must be fed by hand, a particular problem when laser printers are centrally located and shared by a work group. Also, in order for an envelope to fit in a laser printer and/or to feed properly without skewing, it must be fed lengthwise, which requires that the address information print in "landscape" orientation (90° to the text on the accompanying letter). The styles available for "landscape" printing are usually very limited and more often than not, the address must be printed in a style and/or size different from the letter itself. Thus, addressing envelopes has become a problem.

One solution to this problem, of course, is to have an ordinary typewriter available to type addresses. This solution is not satisfactory, however, since the space around secretarial desks is usually at a premium, and matching typestyles is difficult. Feeding sheets of adhesive-backed labels through a laser printer is not a practical solution either, since a single address label is too small to feed properly and it is usually inconvenient to collect and print a number of addresses simultaneously on a sheet of labels. Using adhesive-backed labels is particularly inconvenient when the printer is shared and is not located at the user's desk. Prior to the present invention there did not seem to be a good solution to the problem.

The invented Image Transfer Label provides a fast and convenient way of applying an address to a business envelope where the original letter is produced by a laser printer or some other similar printing system, such as a xerographic reproduction system.

SUMMARY OF THE INVENTION

The present invention is described in the context of an address label for envelopes, but other applications for the invention will no doubt occur to those skilled in the art. For example, U.S. Pat. No. 3,973,788 describes a requirement of the Federal Highway Administration for labels which must be legible for the life of a vehicle. Such labels can conveniently and economically be made using the principles of the present invention.

The present invention involves transferring the fused toner image from an address printed on a carrier sheet (typically an ordinary sheet of paper) to the bottom surface of a transparent label, using adhesive or chemical transfer means, and then affixing the transparent label to the envelope by adhesive means. The carrier sheet can be a second copy of the first page of the letter to be sent (either printed as a duplicate original or xerographically reproduced), or possibly a special address page run through the laser printer. After the address is transferred to the transparent label, the carrier sheet may be discarded.

Preferably the transparent label has a peripheral area coated with a contact adhesive which is suitable for permanently adhering the label to an envelope when the label is put in place. This peripheral area is initially covered by a protective sheet which is removed prior to adhering the label to the envelope. The central area of the label has either a film coating which will adhere to fused toner and remove it from the carrier sheet, or it includes chemical means which will cause the fused toner image on the carrier sheet to migrate to the label. Micro-encapsulated solvents may be used to improve the efficacy of image lifting.

BRIEF DESCRIPTION OF THE DRAWINGS

FIG. 1 is a perspective view of the underside of a label according to the present invention showing the removable protective sheets which cover both the peripheral and the central areas of the label partially peeled off.

FIG. 2 is a cross sectional view taken at 2—2 of FIG. 1.

FIG. 3 shows a label according to the present invention positioned over the address area of a carrier sheet in position for transferring the address to the label.

FIG. 4 shows an address label of the present invention as applied to an envelope.

FIG. 5 is a cross sectional view of a pad of image transfer labels taken at the same section as FIG. 2, the pad consisting of three labels.

DETAILED DESCRIPTION OF THE INVENTION

Referring to FIGS. 1 and 2, a transparent label 10 can be seen which has a peripheral adhesive coating 11 whose ultimate purpose is to adhere the label to an envelope. The adhesive coating 11 is protected by a protective sheet 12 which is peeled off the label just before applying the label to the envelope. The central area of the label is treated in one of several ways to enable the lifting of fused toner from a carrier sheet. In one embodiment of the invention, the central area is coated with an adhesive film 13 similar to that on the peripheral area. A somewhat less aggressive adhesive is preferred for the central area, however. The adhesive film on the periphery is preferably one which will hold the label onto the envelope tightly without danger of its peeling off during mailing. Such an adhesive will generally be one which tends to tear the paper somewhat when it is removed. The adhesive for removing toner from the carrier sheet, on the other hand should be one which has sufficient adhering power to remove toner from the carrier sheet, but not so much as to tear the carrier sheet. The central area of the label may also be covered with a peelable protective sheet 14. If so, the protective sheets 12 and 14 are preferably formed from a single sheet which is die cut to form two separate pieces. Such peelable protective sheets are common in the label art and need not be described here in further detail.

To prepare a mailing label according to the present invention, first a carrier sheet 15 containing the desired address is prepared. This can be done by simply laser printing a second copy of the first page of the letter being sent, making a xerographic copy of the first page, or printing a separate page which contains only the address. A blank label, with protective sheet 14 removed is positioned over the address as shown in FIG. 3. As shown in FIG. 3, the top surface of the label as seen in FIG. 1 is against the sheet 15. The dotted line 18 which is seen in the figure represents the opening in protective sheet 12 which is on the underside of label 10. The central area of the label is then rubbed slightly so that the adhesive 13 makes intimate contact with the fused toner image which is the desired address. As the label is removed from the carrier sheet 15, toner sticks to the adhesive 12 and is thereby peeled from the carrier sheet. Protective sheet 12 is then peeled from the label and the label applied to the envelope 16 as shown in FIG. 4. Since the label 10 is transparent, the address shows through, and since the image is adhered to the back surface of the label, it is protected from damage during mailing.

If it is intended to use the invented label on large manila envelopes, it may be convenient to make the label somewhat larger than is necessary to display the destination address so that a return address can be preprinted on it.

The toner lift-off film 13 may be in the form of a contact adhesive as described above, or it may take other forms. For example, many typewriters incorporate a special "correcting" ribbon which is used to correct errors. The lift-off medium used in these ribbons is typically a micro-encapsulated adhesive. These ribbons, while possibly requiring more rubbing to transfer the image, are also suitable for use in connection with this invention. Also, I have discovered that polyvinyl chloride sheet stock can be used (without a coating) to lift off fused toner images with the application of heat. Apparently the plasticizer in the vinyl acts as a kind of controlled release solvent which bonds the toner strongly to the vinyl, thereby causing it to lift the image off the carrier sheet as the vinyl sheet is removed.

The efficacy of the lift-off medium may be improved by using micro-encapsulated solvents on the lift-off film to help loosen the toner bond to the carrier sheet. The strength of the toner bond depends, of course, on the amount of fusing. If the carrier sheet image is not fused, or if the fusing is incomplete, the transfer process will be considerably easier to accomplish.

If the image lift-off means used has little or no adhesive properties, it is preferred that the peripheral adhesive region 11 extend slightly into the central area of the label so as to hold the label in position on the carrier sheet while the image transfer process is taking place. The incursion into the central area should be small enough that paper tearing does not become a problem. It is also possible to coat at least a portion of the central area with a removable contact adhesive film whose primary function is to hold the label in place on the carrier sheet while the toner lift-off means causes the toner to transfer. Hence numeral 13 should be understood to refer to a toner lift-off film alone (which may or may not be adhesive) or a combination of a lift-off film and an adhesive. An adhesive in the central area can also serve to pad blank labels in a mahner similar to the way that pads of notepaper are formed. That is, a pad of labels, without protective sheets 14, can be made by stacking labels so that the adhesive in the central area of one label is adhered to the opposite surface (17) of the next label in the stack. The protective function of sheet 14 is thus served by the next lower label in the pad. To use, the top label in the pad is simply peeled off the pad and then applied to the carrier sheet as explained above. The central area of the bottom label in said pad is preferably protected, as by a sheet 14.

While the foregoing describes the invention according to the presently preferred embodiments, persons skilled in the art will no doubt be enabled to make various adaptations and modifications of the invention, which adaptations and modifications are intended to fall within the spirit of the following claims.

I claim:

1. A label comprising:
(a) a transparent substrate, the surface area on one side of said substrate being divided into first and second areas;
(b) a coating of adhesive on said first area;
(c) means comprising a first removable protective sheet covering said first area but not said second area to permit handling of said label without touching either said first or second area; and
(d) means comprising a layer of adhesive and micro-encapsulated solvent disposed on said second area for lifting toner off a carrier sheet.

2. A label as recited in claim 1 where said first area comprises a border around the periphery of said substrate enclosing said second area.

3. A label as recited in claim 1 and further including a second removable protective sheet covering said second area.

4. A label as recited in claim 3 wherein said first area comprsies a border around the periphery of said substrate enclosing said second area.

5. An image transfer medium for transferring an image from a first surface to a second surface which comprises:
(a) a transparent substrate;
(b) image lift-off means comprised of a coating of micro-encapsulated solvent and adhesive covering an area of one surface of said surface; and
(c) means for attaching said substrate to said second surface.

6. An image transfer medium as recited in claim 5 where said means for attaching said substrate to said second surface comprises an adhesive coating on at least a portion of said one surface of said substrate.

7. An image transfer medium as recited in claim 6 where the adhesive of said image lift-off means and the adhesive coating comprising said means for attaching said substrate to said second surface are the same substance.

8. An image transfer medium for transferring an image from a first surface to a second surface which comprises:
(a) a transparent substrate;
(b) image lift-off means comprising
  (i) a layer of adhesive disposed on an area of one surface of said substrate and
  (ii) a coating of micro-encapsulated solvent adhered to said adhesive; and
(c) means for attaching said substrate to said second surface.

9. An image transfer medium as recited in claim 8 where said attaching means comprises an adhesive covering at least a portion of the surface of said substrate containing said image lift off means, and further including a removable protective covering over at least a portion of said attaching means to permit handling without touching said attaching means.

* * * * *